United States Patent [19]
Lum et al.

[11] Patent Number: 6,117,887
[45] Date of Patent: Sep. 12, 2000

[54] INHIBITION OF 26S AND 20S PROTEASOME BY INDANONES

[75] Inventors: Robert T. Lum, Palo Alto; Steven R. Schow, Redwood City; Alison Joly, San Mateo, all of Calif.; Suresh Kerwar, Westchester, N.Y.; Marek G. Nelson, Sunol, Calif.; Michael M. Wick, Chestnut Hill, Mass.

[73] Assignee: CV Therapeutics, Inc., Palo Alto, Calif.

[21] Appl. No.: 09/088,581

[22] Filed: Jun. 2, 1998

Related U.S. Application Data

[63] Continuation of application No. 08/719,042, Sep. 24, 1996, Pat. No. 5,834,487.

[51] Int. Cl.[7] ........................ A61K 38/00; A61K 31/445; A61K 31/95
[52] U.S. Cl. .......................... 514/319; 514/19; 514/561; 514/677
[58] Field of Search .............................. 514/319, 19, 561, 514/677

[56] References Cited

U.S. PATENT DOCUMENTS

| 5,409,944 | 4/1995 | Black et al. . |
| 5,457,237 | 10/1995 | Dow . |

FOREIGN PATENT DOCUMENTS

| 0 356 247 A1 | 8/1989 | European Pat. Off. . |
| WO 92/00961 | 1/1992 | WIPO . |
| WO 95/24914 | 3/1995 | WIPO . |
| WO 95/25533 | 3/1995 | WIPO . |

OTHER PUBLICATIONS

Coux et al., *Annu. Rev. Biochem.*, vol. 65, pp. 801–847, Structure and Functions of the 20S and 26S Proteasomes (1996).

Löwe et al., *Science*, vol. 268, pp. 533–539, Research Article, Crystal Structure of the 20S Proteasome from the Archaeon *T. acidophilum* at 3.4 Å Resolution (1995).

Dahlmann et al., *FEBS Letters*, vol. 251, No. 1,2, pp. 125–131, the Multicatalytic Proteinase (prosome) is Ubiquitous From Eukaryotes to Archaebacteria (1989).

Seemüller et al., *FEBS Letters*, vol. 359, pp. 173–178, The Proteasome From *Thermoplasma Acidophilum* is Neither a Cysteine Nor a Serine Protease (1995).

Orlowski, *Biochemistry*, vol. 29, No. 45, pp. 10289–10297, The Multicatalytic Proteinase Complex, a major Extralysosomal Proteolytic System (1990).

Orlowski et al., *Biochemistry*, vol. 32, pp. 1563–1572, Evidence for the Presence of Five Distinct Proteolytic Components in the Pituitary Multicatalytic Proteinase Complex. Properties of Two Components Cleaving Bonds on the Carboxyl Side of Branched Chain and Small Neutral Amino Acids (1993).

Vinitsky et al., *Biochemistry*, vol. 31, pp. 9421–9428, Inhibition of the Chymotrypsin–like Activity of the Pituitary Multicatalytic Proteinase Complex (1992).

Tsubuki et al., *Biochemical and Biophysical Research Communications*, vol. 196, No. 3, pp. 1195–1201, Purification and Characterization of a Z–Leu–Leu–Leu–MCA Degrading Protease Expected to Regulate Neurite Formation: A Novel Catalytic Activity in Proteasome (1993).

Rock et al., *Cell*, vol. 78, pp. 761–771, Inhibitors of the Proteasome Block the Degradation of Most Cell Proteins and the Generation of Peptides Presented on MHC Class I Molecules (1994).

Iqbal et al., *J. Med. Chem.*, vol. 38, pp. 2276–2277, Potent Inhibitors of Proteasome (1995).

Iqbal et al., *Bioorganic & Medicinal Chemistry Letters*, vol. 6, No. 3, pp. 287–290, Potent –Ketocarbonyl and Boronic Este Derived Inhibitors of Proteasome (1996).

Fenteany et al., *Science*, vol. 268, pp. 726–731, Inhibition of Proteasome activities and Subunit–Specific Amino–Terminal Threonine Modification by lactacystin (19950.

Omura et al., *The Journal of Antibiotics*, vol. 44, No. 1, pp. 117–118, Structure of Lactacystin, A New Microbial Metabolite Which Induces Differrentiation of Neuroblastoma Cells (1990).

Fenteany et al., *Proc. Natl. Acad., Sci, USA*, vol. 91, pp. 3358–3362, Aβ–Lactone Related to Lactacystin Induces Neurite Outgrowth in a Neuroblastoma Cell Line and Inhibits Cell Cycle Progression in an Osteosarcoma Cell Line (1994).

Ciechanover, *Cell*, vol. 79, pp. 13–21, The Ubiquitin–Proteasome Proteolytic Pathway (1994).

Palombella et al., *Cell*, vol. 78, pp. 773–785, The Ubiquitin–Proteasome Pathway is Required for Processing the NF–κB1 Precursor Protein and the Activation of NF–κB (1994).

Ko et al., *Genes & Development*, vol. 10, pp. 1054–1072, p53: Puzzle and Paradigm (1996).

Oren, *Seminars on Cancer Biology*, vol. 5, pp. 221–227, Relationship of p53 to the Control of Apoptotic Cell Death (1991).

*Primary Examiner*—James H. Reamer
*Attorney, Agent, or Firm*—McDonnell Boehnen Hulbert & Berghoff

[57] ABSTRACT

This invention is novel indanone compositions useful for inhibiting cell proliferation disorders in mammals.

9 Claims, 3 Drawing Sheets

INHIBITION OF 26S AND 20S PROTEASOME BY INDANONES

This is a continuation of U.S. patent application Ser. No. 08/719,042, filed on Sep. 24, 1996, now U.S. Pat. No. 5,834,487.

BACKGROUND OF THE INVENTION

1. Field of Invention

This invention is a method for inhibiting cell proliferation using a class of indanone compositions never before considered for that purpose. As inhibitors of cell proliferation, the compositions are useful in the treatment of cancer, cardiovascular disease, e.g. restenosis, host graft rejection, gout, and other proliferative disorders as well as being potential therapeutics for autoimmune diseases, such as rheumatoid arthritis, lupus, type I diabetes, multiple sclerosis and similar disorders and diseases.

2. Description of the Art

The multicatalytic proteinase or proteasome is a highly conserved cellular structure that is responsible for the ATP-dependent proteolysis of most cellular proteins. The 20S (700-kDa) proteasome contains at least five distinct proteolytic activities that have a new type of mechanism involving a threonine residue at the active site (Coux, O., Tanaka, K. and Goldberg, A. 1996 Ann. Rev. Biochem. 65:801–47).

The 20S proteasome has been crystallized from the archaebacteria *Thermoplasma acidophilum* (Lowe, J., Stock, D., Jap. B., Zwickl, P., Bauminster, W., and Huber, R. 1995 Science 268:533–539). The archaebacterial 20S proteasome contains fourteen copies of two distinct types of subunits, α and β, which form a cylindrical structure consisting of four stacked rings. The top and bottom rings contain seven α subunits each whilst the inner rings contain seven β subunits. A pore extends through the middle of the structure that contains the proteolytic active sites and proteins destined for degradation pass through this channel. The eukaryotic 20S proteasome is more complex than that of the archaebacteria because the number of distinct subunits has increased during evolution, however, the subunits can still be classed according to the α and β nomenclature of archaebacteria according to their homology. Thus the quaternary structure of the eukaryotic complex is similar to that of the archaebacteria being comprised of two α and two β rings. However, unlike the archaebacterial proteasome that primarily exhibits chymotrypsin-like proteolytic activity (Dahlmann, B., Kopp, F., Kuehn, L., Niedel, B., Pfeifer, G. 1989 FEBS Lett. 251:125–131, Seemuller, E., Lupas, A., Zuhl, F., Zwickl, P and Baumeister, W. 1995 FEBS Lett. 359:173; and Lowe, J., Stock, D., Jap, B., Zwickl, P., Bauminster, W. and Huber, R. 1995 Science 268:533–539), the eukaryotic proteasome contains at least five identifiable protease activities. These are termed chymotrypsin-like, trypsin-like and peptidylglutamyl-peptide hydrolyzing. Two other activities have also been described, one exhibiting a preference for cleavage of peptide bonds on the carboxyl side of branched chain amino acids and the other toward bonds between small neutral amino acids. (Orlowski, M. 1990 Biochemistry 29: 10289–10297).

Although the 20S proteasome contains the proteolytic core, it cannot degrade proteins in vivo unless it is complexed with a 19S cap at either end of its structure, which itself contains multiple ATPase activities. This larger structure is known as the 26S proteasome and rapidly degrades proteins that have been targeted for degradation by the addition of multiple molecules of the 8.5-kDa polypeptide, ubiquitin.

The first step towards the ubiquitination of a protein proceeds by activation of a ubiquitin molecule at its carboxyl terminal glycine residue by addition of ATP that creates a high energy thioester intermediate. This step is catalyzed by the ubiquitin-activating enzyme, E1. Ubiquitin is then transferred to the active cysteine residue of a ubiquitin-conjugating enzyme, E2. E2 enzymes attach ubiquitin to the E-amino groups of lysine residues on the substrate protein that is destined to be degraded. This process, in some cases also requires a ubiquitin ligase, E3. Repeated conjugation of ubiquitin to lysine residues of formerly bound ubiquitin moieties leads to the formation of multi-ubiquitin chains and creates a scaffold of ubiquitin around the substrate protein. Multi-ubiquitinated substrate proteins are recognized by the 26S proteasome and are degraded and the multi-ubiquitin chains are released from the complex and ubiquitin is recycled.

What causes a protein to become ubiquitinated and thus degraded is still under investigation. Clearly this must be a highly regulated series of events since the critical timing of specific protein degradation is crucial for many cell cycle functions. Several signals have been proposed which largely center upon internal structural sequences within the substrate itself. One such proposal is the "N-end rule" in which the amino terminal residue of a protein determines it's half life. Other proteins such as the cyclins contain a short sequence of highly conserved amino acids termed the "destruction box" that are apparently necessary for degradation. Furthermore "PEST" sequences, which consist of regions rich in proline, aspartate, glutamate, serine and threonine also seem to act as degradation signals. It is thought that such internal sequences act as recognition elements between the protein substrate and its specific ubiquitination machinery.

Two types of inhibitors that inhibit the proteolytic activity of the proteasome, have been described. Certain peptide aldehydes have been reported to inhibit the chymotrypsin-like activity associated with the proteasome (Vinitsky, A., Michaud, C., Powers, J. and Orlowski, M. 1992 Biochemistry 31:9421–9428; Tsubuki, S., Hiroshi, K., Saito, Y., Miyashita, N., Inomata, M., and Kawashima, S., 1993 Biochem.Biophys.Res.Commun. 196:1195–1201; Rock, K, l., Gramm, C., Rothstein, L., Clark K., Stein, R., Dick, L., Hwang, D., and Goldberg, A. L. 1994 Cell 78:761–771). These are N-acetyl-L-leucinyl-L-leucinal-L-norleucinal (ALLN) and a closely related compound, N-acetyl-L-leucinyl-L-leucinyl-methional (LLM) with a $K_i$'s of 0.14 $\mu$M. The most potent inhibitor of this type is a structurally related compound, N-carbobenzoxyl-L-leucinyl-L-leucinyl-L-norvalinal (MG 115) which exhibits a $K_i$ of 0.021 $\mu$M. Although these peptide aldehydes are most effective against the chymotrypsin-like proteolytic activity of the proteasomes, careful studies have shown that they are non-specific protease inhibitors. More recent reports have described series of potent dipeptide inhibitors that have $IC_{50}$ values in the 10–100 nM range in vitro (Iqbal, M., Chatterjee, S., Kauer, J. C., Das, M., Messina, P., Freed, B., Biazzo, W., and Siman, R. 1995 J.Med.Chem. 38:2276–2277) and a series of similarly potent in vitro inhibitors from α-ketocarbonyl and boronic ester derived dipeptides (Iqbal, M., Chatterjee, S., Kauer, J. C., Mallamo, J. P., Messina, P. A., Reiboldt, A., and Siman, R. 1996 Bioorg. Med.Chem. Lett 6:287–290).

Another report describes a class of compounds that exhibit specificity in inhibiting proteasome activity (Fenteany, G., Standaert, R. F., Lane, W. S., Choi, S., Corey, E. J., and Schreiber, S. L. 1995 Science 268:726–731).

Lactacystin is a Streptomyces metabolite that specifically inhibits the proteolytic activity of the proteasome complex. This molecule was originally discovered for its ability to induce neurite outgrowth in a neuroblastoma cell line (Omura et al., 1991 J.Antibiot. 44:113) later it was shown to inhibit the proliferation of several cell types (Fenteany et al 1994 Proc.Nat'l. Acad.Sci. USA 91: 3358). By using radio-labelled lactacystin, binding studies by (Fenteany et al., 1995 Science 268:726–731) have identified the binding site and the mechanism of action. These studies have shown that lactacystin binds irreversibly to a threonine residue located at the amino terminus of the β subunit of the proteasomes. A series of analogues based upon the structure of lactacystin were also investigated (Fenteany et al., 1995 Science 268:726–731). These studies indicated that the β-lactone structure was essential for its inhibitory activity.

It is now well established that the proteasome is a major extralysosomal proteolytic system which is involved in the degradative pathways resulting in numerous and diverse cellular functions such as cell division, antigen processing and the degradation of short lived regulatory proteins such as transcription factors, oncogene products and cyclins (reviewed in Ciechanover, A. 1994 Cell 79:13–21). The primary function of the proteasome is to catalyze the proteolysis of proteins into small peptides. However, it has also been demonstrated that the ubiquitin-proteasome pathway can catalyze the regulated proteolytic processing of a large inactive precursor into an active protein. The best documented case of this involves the activation of the transcription factor NF-κB (Palombella, V. J., Rando, O. J., Goldberg, A. L., and Maniatis, T. 1994 Cell 78:773–785). The active form of NF-κB is a heterodimer consisting of a p65 and a p50 subunit. The latter is present in the cytosol of the cell in an inactive precursor form, namely p105, the 105-kDa polypeptide precursor of p50. The proteolytic processing of p105 to generate p50 occurs via the ubiquitin-proteasome pathway. Additionally, processed p50 and p65 is maintained in the cytosol as an inactive complex with the inhibitory protein IκB. Inflammatory signals activate NF-κB by initiating the signalling pathway for the complete degradation of IκB, and also stimulate the processing of p105 into p50. Thus two proteolytic events, both governed by the ubiquitin-proteasome pathway, are required for signal induced activation of NF-κB. What causes the termination of proteolysis of p105 following generation of p50 is not known but it has been proposed that the conformation of p50 may render it resistant to further processing and cause it to dissociate from the 26S complex.

The fact that the proteasome plays a critical event in the activation of NF-κB could be exploited clinically by the use of inhibitors directed towards proteasome proteolysis. In certain diseases the normal function of active NF-κB can be detrimental to human health as observed in inflammatory responses following bacterial, fungal or viral infection. Thus inhibitors of NF-κB activation, due to their ability to prevent secretion of cytokines, may have potential utility in the treatment of ARDS (acute respiratory distress syndrome) and AIDS. Since activation of NF-κB is also essential for angiogenesis, proteasome inhibitors may have utility in the treatment of those diseases associated with abnormal neovascularization.

p53 was first described as an oncoprotein but has since been shown to be involved in many cellular processes (reviewed by Ko, L. J. and Proves, C. 1996 *Genes Dev.* 10, 1054–1072). p53 has been shown to induce apoptosis in several haematopoietic cell lines (Oren, M., 1994 *Semin. Cancer Biol.* 5, 221–227) through the action of many different stimuli including DNA damage, viral infection and the removal of growth factors. However, it is important to note that apoptosis can be induced in a p53-independent manner for example by the action of glucocorticoids. Induction of p53 leads to cell growth arrest in the G1 phase of the cell cycle as well as cell death by apoptosis. Both of these functions allow p53 to control DNA damage thereby reducing the propagation of DNA mutations when cells divide. p53 arrests cells at G1 by inducing the cyclin-dependent kinase inhibitor, p21, which in turn causes an accumulation of the hypophosphorylated form of the retinoblastoma gene product. It is thought that p53 acts as a check point in the cell following DNA damage, it first causes an arrest in cell division and apoptosis. p53 degradation is known to be via the ubiquitin-proteasome pathway and disrupting p53 degradation is a possible mode of inducing apoptosis. Another potential utility of proteasome inhibitors may be in the treatment of diseases that result from abnormal cell proliferation.

It is well documented that the ubiquitin-proteasome pathway is critical for the regulated destruction of cyclins that govern the exit from mitosis and allow cells to progress into the next phase of the cell cycle. Thus inhibiting degradation of cyclins by using proteasome inhibitors causes growth arrest. Therefore another potential utility of proteasome inhibitors is their use in the treatment of diseases that result from an accelerated cell division. These include cancer, cardiovascular diseases such as myocarditis, restenosis following angioplasty, renal diseases such as lupus, polycystic kidney disease, fungal infections, dermatological diseases such as psoriasis, abnormal wound healing, keloids, immunological diseases such as autoimmunity, asthma, and allergy, acute and delayed hypersensitivity, graft versus host disease, transplant rejection and neuroimmunological diseases such as multiple sclerosis and acute disseminated encephalomyelitis.

SUMMARY OF THE INVENTION

It is an object of this invention to provide a method for inhibiting cell proliferation in mammals that uses a therapeutically effective amount of a composition heretofore unknown for its cell proliferative inhibition properties.

It is an object of this invention to provide a method for the effective treatment of diseases that result from accelerated cell division.

It is another object of this invention to provide a method for the treatment of proliferative diseases that operates by inhibiting the degradation of proteasome inhibitors.

It is another object of this invention to use a therapeutically effective amount of the composition to inhibit cell proliferative disorders in humans.

In one embodiment, this invention is a method for inhibiting cell proliferation in mammals comprising administering to the mammal a therapeutically effective amount of a compound having the formula:

In the compound, $R_1$–$R_4$ are each individually selected from the group including hydrogen, halogen, hydroxyl, thiol, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

$R_5$–$R_9$ are each individually selected from the group of compounds including hydrogen, halogen, hydroxyl, thiol, oxo, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;

X is selected from the group of compounds including hydrogen, -$D_1$, -$D_2$, -E, -$D_1$-E, -$D_2$-E, -$D_1$–$D_2$ or a compound having the formula:

wherein $D_1$ and $D_2$ are each individually selected from the group of compounds including a compound having the formula:

or hydrogen, halogen, hydroxyl, thiol, lower alkyl, substituted lower alkyl, alkynyl, alkyl alkenyl, alkyl alkynyl, alkoxy, alkylthio, acyl, aryloxy, amino, amido, carboxyl, aryl, substituted aryl, heterocycle, heteroaryl, substituted heterocyclic, heteroalkyl, cycloalkyl, substituted cycloalkyl, alkylcycloalkyl, or alkylcycloheteroalkyl;

wherein E is selected from the group of compounds including:

or hydrogen, halogen, hydroxyl, thiol, lower alkyl, substituted lower alkyl, alkynyl, alkylalkenyl, alkyl alkynyl, alkoxy, alkylthio, acyl, aryloxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, or alkylcycloheteroalkyl.

When $D_1$, $D_2$ and/or E are selected from compounds including substituents $R_{10}$–$R_{14}$, $J_1$ and $J_2$, then $R_{10}$–$R_{14}$ are each individually selected from the group of compounds including hydrogen, halogen, hydroxyl, thiol, oxo, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano and $J_1$ and $J_2$ are each individually selected from the group of compounds including N—$R_{15}$, $CR_{16}R_{17}$, O, S—$(O)_{0-2}$, P—$(O)_{0-3}$, wherein $R_{15}$–$R_{17}$ may each be individually selected from the group of compounds including hydrogen, halogen, hydroxyl, oxo, thiol, lower alkyl, substituted lower alkyl, alkynyl, alkylalkenyl, alkyl alkynyl, alkoxy, alkylthio, acyl, aryloxy, amino, amido, carboxyl, aryl, substituted aryl, heterocyclic, heteroaryl, substituted heterocycle, heteroalkyl, cycloalkyl, substituted cycloalkyl, alkylcycloalkyl, alkylcycloheteroalkyl, or cyano.

The compositions are useful, when administered in therapeutic amounts, for treating mammals, and preferably for treating humans suffering from cell proliferative disorders, infectious diseases, inflammation, and immunological diseases.

DESCRIPTION OF THE FIGURES

In the Figures.

DESCRIPTION OF THE CURRENT EMBODIMENT

This invention is a method for inhibiting cell proliferation disorders, infectious diseases, and immunological diseases in mammals and especially in humans using compositions having the following general formula:

In the composition, $R_1$–$R_4$ are each individually selected from the group of compounds including hydrogen, halogen, hydroxyl, thiol, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In the composition, $R_5$–$R_9$ are each individually selected from the group of compounds including hydrogen, halogen, hydroxyl, thiol, oxo, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

X is selected from the group of compounds including hydrogen, $-D_1$, $-D_2$, $-E$, $-D_1-D_2$, $-D_1-E_1$, $-D_2-E$ or a compound having the formula:

wherein $D_1$ and $D_2$ are each each individually selected from the group of compounds including hydrogen, halogen, hydroxyl, thiol, lower alkyl, substituted lower alkyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocyclic, heteroalkyl, cycloalkyl, substituted cycloalkyl, alkylcycloalkyl, or alkylcycloheteroalkyl; and wherein E is selected from the group of compounds including:

hydrogen, halogen, hydroxyl, thiol, lower alkyl, substituted lower alkyl, alkynyl, alkylalkenyl, alkyl alkynyl, alkoxy, alkylthio, acyl, aryloxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, or alkylcycloheteroalkyl.

In the compounds identified above, $R_5-R_9$ are each individually selected from the group of compounds including hydrogen, halogen, hydroxyl, thiol, oxo, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

When $D_1$, $D_2$ and/or E are selected from compounds including substituents $R_{10}-R_{14}$ $J_1$ and $J_2$, then: $R_{10}-R_{14}$ are each individually selected from the group of compounds including hydrogen, halogen, hydroxyl, thiol, oxo, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano; and $J_1$ and $J_2$ are each individually selected from the group including $N-R_{15}$, $CR_{16}R_{17}$, O, $S-(O)_{0-2}$, $P-(O)_{0-3}$, wherein $R_{15}-R_{17}$ are each individually substituted with a component selected from the group including hydrogen, halogen, hydroxyl, oxo, thiol, lower alkyl, substituted lower alkyl, alkynyl, alkylalkenyl, alkyl alkynyl, alkoxy, alkylthio, acyl, aryloxy, amino, amido, carboxyl, aryl, substituted aryl, heterocyclic, heteroaryl, substituted heterocycle, heteroalkyl, cycloalkyl, substituted cycloalkyl, alkylcycloalkyl, alkylcycloheteroalkyl, or cyano.

The following terms are used to describe various constituents of the chemical composition useful in the method of this invention. The terms are defined as follows:

The term "halogen" refers to fluorine, bromine, chlorine, and iodine atoms.

The term "hydroxyl" refers to the group —OH.

The term "oxo" refers to the group =O.

The term "thiol" or "mercapto" refers to the group —SH, and $—S(O)_{0-2}$.

The term "lower alkyl" refers to a cyclic, branched or straight chain, alkyl group of one to ten carbon atoms. This term is further exemplified by such groups as methyl, ethyl, n-propyl, I-propyl, n-butyl, t-butyl, I-butyl (or 2-methylpropyl), cyclopropylmethyl, I-amyl, n-amyl, hexyl and the like.

The term "substituted lower alkyl" refers to lower alkyl as just described including one or more groups such as hydroxyl, thiol, alkylthiol, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, cyano. These groups may be attached to any carbon atom of the lower alkyl moiety.

The term "alkenyl" refers to a group —CR'=CR"R'" where R', R", R'" are each selected from hydrogen, halogen, lower alkyl, substituted lower alkyl, acyl, aryl, substituted aryl, heteroaryl, substituted heteroaryl or the like as defined.

The term "alkynyl" refers to a group —C≡C—R'; where R' is selected from hydrogen, halogen, lower alkyl, substituted lower alkyl, acyl, aryl, substituted aryl, heteroaryl, substituted heteroaryl or the like as defined.

The term "alkyl alkenyl" refers to a group -R—CR'=CR'"R"", where R is lower alkyl, or substituted lower alkyl, R', R'", R"" are each independently selected from hydrogen, halogen, lower alkyl, substituted lower alkyl, acyl, aryl, substituted aryl, hetaryl, or substituted hetaryl as defined below.

The term "alkyl alkynyl" refers to a group -RC≡CR' where R is lower alkyl or substituted lower alkyl, R' is hydrogen, lower alkyl, substituted lower alkyl, acyl, aryl, substituted aryl, hetaryl, or substituted hetaryl as defined below.

The term "alkoxy" refers to the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined below.

The term "alkylthio" denotes the group —SR, $—S(O)_{n=1-2}$—R, where R is lower alkyl, substituted lower alkyl, aryl, substituted aryl aralkyl or substituted aralkyl as defined below.

The term "acyl" refers to groups —C(O)R, where R is hydrogen, lower alkyl substituted lower alkyl, aryl, substituted aryl and the like as defined below.

The term "aryloxy" refers to groups —OAr, where Ar is an aryl, substituted aryl, heteroaryl, or substituted heteroaryl group as defined below.

The term "amino" refers to the group NRR', where R and R' may independently be hydrogen, lower alkyl, substituted lower alkyl, aryl, substituted aryl, hetaryl, cycloalkyl, or substituted hetaryl as defined below or acyl.

The term "amido" refers to the group —C(O)NRR', where R and R' may independently be hydrogen, lower alkyl, substituted lower alkyl, aryl, substituted aryl, hetaryl, substituted hetaryl as defined below.

The term "carboxyl" refers to the group —C(O)OR, where R may independently be hydrogen, lower alkyl, substituted lower alkyl, aryl, substituted aryl, hetaryl, substituted hetaryl and the like as defined.

The terms "aryl" or "Ar" refer to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl).

The term "substituted aryl" refers to aryl optionally substituted with one or more functional groups, e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The terms "heteroaryl" or "hetar" refer to a heterocycle in which at least one heterocyclic ring is aromatic.

The term "substituted heteroaryl" refers to a heterocycle optionally mono or poly substituted with one or more functional groups, e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "aralkyl" refers to the group -R-Ar where Ar is an aryl group and R is lower alkyl or substituted lower alkyl group. Aryl groups can optionally be unsubstituted or substituted with, e.g., halogen, lower alkyl, alkoxy, alkyl thio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "heteroalkyl" refers to the group -R-Het where Het is a heterocycle group and R is a lower alkyl group. Heteroalkyl groups can optionally be unsubstituted or substituted with e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "heteroarylalkyl" refers to the group -R-HetAr where HetAr is an heteroaryl group and R lower alkyl or substituted loweralkyl. Heteroarylalkyl groups can optionally be unsubstituted or substituted with, e.g., halogen, lower alkyl, substituted lower alkyl, alkoxy, alkylthio, aryl, aryloxy, heterocycle, hetaryl, substituted hetaryl, nitro, cyano, alkylthio, thiol, sulfamido and the like.

The term "cycloalkyl" refers to a divalent cyclic or polycyclic alkyl group containing 3 to 15 carbon For polycyclic groups, these may be multiple condensed rings in which one of the distal rings may be aromatic (e.g., indanyl, tetrahydronaphthalene, etc. . . . ).

The term "substituted cycloalkyl" refers to a cycloalkyl group comprising one or more substituents with, e.g., halogen, lower alkyl, substituted lower alkyl, alkoxy, alkylthio, aryl, aryloxy, heterocycle, hetaryl, substituted hetaryl, nitro, cyano, alkylthio, thiol, sulfamido and the like.

The term "cycloheteroalkyl" refers to a cycloalkyl group wherein one or more of the ring carbon atoms is replaced with a heteroatom (e.g., N, O, S or P).

The term "substituted cycloheteroalkyl" refers to a cycloheteroalkyl group as herein defined which contains one or more substituents, such as halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "alkyl cycloalkyl" refers to the group -R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "amino acid" refers to the D- or L-isomer of naturally occurring and synthetic alpha amino acids preferably the amino acids are naturally occurring alanine, arginine, asparagine, aspartic acid, cysteine, glutamine, glutamic acid, glycine, histaidine, isoleucine, leucine, lysine, methionine, phenylalanine, proline, serine, threonine, tryptophan, tyrosine or valine.

Typically $D_1$, $D_2$ and E, if present in the composition, may be amino acids. Usually lipophilic amino acids are preferred. In general, the amino acid abbreviations follow the IUPAC-IUB Joint Commission on Biochemical Nomenclature as described in Eur. J. Biochem, 158, 9(1984).

It is preferred that $R_3$ is methoxy, $-D_1$ is leucine, and $-D_2$ is leucine, and E is NR'R". It is most preferred that $-D_1$ is l-leucine, and $-D_2$ is d-leucine and that E is selected from the group of compounds consisting of benzylamine, 1-indanylamine, N,N'-dibenzylamine, 2,6-difluorobenzylamine, 4-methoxybenzylamine, piperonyl amine, $NH_2$ and glycineamide.

In one preferred composition, $R_3$ is methoxy, $D_1$ is leucine, $D_2$ is leucine, and E is benzylamine. In another preferred composition, $R_3$ is methoxy, $D_1$ is leucine, $D_2$ is leucine, and E is 1-indanylamine. In still another preferred composition, $R_3$ is methoxy, $D_1$ is leucine, $D_2$ is leucine, and E is N,N-dibenzylamine. In another preferred composition, $R_3$ is methoxy, $D_1$ is leucine, $D_2$ is leucine, and E is 2,6-difluorobenzylamine.

In these preferred compositions, it is further preferred that $D_1$ is L-Leucine and $D_2$ is D-Leucine. Known compounds that may be useful in the therapeutic method of this invention are disclosed in Table 1 immediately below.

TABLE 1

| R1 | R2 | R3 | R4 | R5 | R6 | R7 | R8 | R9 | D1 |
|----|----|----|----|----|----|----|----|----|-----|
|  | Cl |  |  | Me |  |  |  |  | OH |
|  |  | OMe | OMe |  |  |  |  | =N—OH | OMe |
|  |  |  |  | Ph |  |  |  |  | Me |
|  | Cl |  |  | Me |  |  |  | =N—OH | OEt |
|  | OMe |  |  |  |  |  |  |  | OH |
|  |  |  |  |  |  |  | Me |  | OMe |
| F |  | F |  |  |  |  |  |  | NH2 |
|  |  |  |  |  |  |  |  |  | NHEt |
|  |  |  |  | Ph |  |  | =CHPh |  | OH |
|  |  | F |  |  |  |  |  |  | OH |
|  |  |  |  |  |  |  |  |  | OH |
|  |  | OMe |  | Me |  |  |  |  | OH |
|  | Me |  |  | Me |  |  |  |  | OH |
|  |  |  |  | Ph |  |  |  | =N—OH | OMe |
|  |  | OMe |  |  |  |  | =CH-(4-dimethylaminophenyl) |  | OH |
|  | OMe |  |  |  |  |  |  | =N—OH | OMe |
|  |  |  |  | Ph |  |  | COOEt |  | Me |
|  |  |  |  | Me |  |  |  | =N—OH | OEt |
|  |  | Me |  |  |  |  |  |  | OMe |
|  |  |  |  |  | Me |  |  |  | OH |
|  | Cl |  |  | Me |  |  | NHCOCOOEt |  | OEt |
|  |  | OMe | OMe |  |  |  |  |  | OH |
|  |  |  |  | Me |  |  |  |  | Me |
| F |  | F |  |  |  |  |  |  | OH |
|  |  |  |  |  |  |  |  |  | NHMe |
|  |  |  |  | Ph |  |  |  |  | OH |
|  |  | OMe |  | Me |  |  |  | =N—OH | OMe |
|  |  | OMe |  |  |  |  |  |  | OH |
|  |  |  |  | Me |  |  | NHAc |  | OMe |
|  |  |  |  |  | Ph |  | Ph |  | OH |
|  |  |  |  | Ph |  |  |  |  | NHCyclopropyl |
|  | OMe | OMe |  |  |  |  |  |  | OH |
|  |  |  |  | Ph |  |  |  |  | OH |
|  |  | COOMe |  |  |  |  |  |  | OMe |
|  | OMe | OMe |  |  |  |  |  | =N—OH | OMe |
|  |  |  |  | Ph |  |  |  |  | OMe |
|  | Cl |  |  | Me |  |  |  |  | OEt |
|  |  | OMe | OME |  |  |  |  |  | OMe |
|  |  |  |  |  |  |  | Me |  | OH |
|  |  |  |  | Me |  |  | NHCOCOOEt |  | OEt |
|  |  |  |  |  |  |  |  |  | NH-n-propyl |
| Ome |  |  | NO2 |  |  |  |  |  | OH |
|  |  | F |  |  |  |  |  |  | Cl |
|  |  | OMe |  |  |  |  |  |  | OMe |
|  |  | OMe |  | Me |  |  |  | =N—OH | OMe |
|  |  | OMe |  | Me |  |  |  |  | OMe |
|  | Me |  |  | Me |  |  |  |  | OMe |
|  |  | F |  |  |  |  | Me |  | OH |
|  |  |  |  |  | 4-Methoxyphenyl |  |  |  | OH |
|  |  |  |  |  |  |  |  | =N—OH | OMe |
|  |  |  |  | Ph | CN |  | COOEt |  | OEt |
|  |  |  |  | Me |  |  |  |  | OH |
|  |  | OMe |  |  |  |  |  |  | OMe |
|  |  |  | OMe |  |  |  |  |  | 4-[[4-(1-methylethyl)-1-piperazinyl]carbonyl]phenoxy |
|  | Cl |  |  | Me |  |  | NH2 |  | OEt |
|  |  | Me |  |  |  |  |  |  | OH |
|  |  |  |  |  |  |  | Me |  | OH |
| F |  | F |  |  |  |  |  |  | Cl |
|  |  |  |  |  |  |  |  |  | OMe |
|  |  |  |  | Ph |  |  |  |  | OH |
|  |  | OMe |  |  |  |  |  | =N—OH | OMe |

TABLE 1-continued

| R1 | R2 | R3 | R4 | R5 | R6 | R7 | R8 | R9 | D1 |
|----|----|----|----|----|----|----|----|----|----|
|    |    |    |    |    | 2-naphthyl |    |    |    | OH |
|    |    | OMe |    | Me |    |    |    |    | OMe |
|    |    |    |    |    | Ph |    | Ph |    | OMe |
|    |    |    |    | Ph |    |    |    |    | NH-n-propyl |
|    |    | Me |    |    |    |    |    | =N—OH | OMe |
|    |    |    |    |    | Ph |    |    |    | OH |
|    |    | OMe |    |    |    |    |    | =N—OH | OMe |
|    |    |    |    | Ph | SH |    | COOEt |    | OH |
|    | Cl |    |    |    | Me |    |    |    | OH |
|    | OMe | OMe |    |    |    |    |    |    | OMe |
|    |    |    |    |    | Me |    |    |    | OH |
|    |    |    |    |    | Me |    | NH2 |    | OEt |
|    |    |    |    |    |    |    |    |    | NH-n-Butyl |
|    | NO2 | OMe |    |    |    |    |    |    | OH |
|    |    | F |    |    |    |    |    |    | NH2 |
|    |    |    |    |    | Me |    |    |    | OH |
|    |    |    |    |    | Ph |    |    |    | OH |
|    |    | OMe |    |    |    |    |    |    | OMe |
| Me |    |    |    |    | Me |    | 3-propanoic acid | 3-propanoic acid | OH |
|    |    |    |    |    | Me |    |    |    | OMe |
| OMe |    |    |    |    | Ph |    |    |    | OH |
|    |    | OMe |    | Ph |    |    |    |    | NHMe |
|    |    |    |    |    | Me |    |    | =N—OH | OMe |
|    |    |    |    | Ph | COOEt |    | COOEt |    | OEt |
|    |    | OMe |    |    | COOMe |    |    |    | OMe |

It is within the knowledge of one of skill in the art that stereoisomers of the compositions described herein as well as isomer and stereoisomers of components that comprise the compositions identified herein all fall within the scope of compositions that are useful in the therapeutic method of this invention.

If the compound useful in the method of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. If the final compound contains an acidic group, cationic salts may be prepared. Typically the parent compound is treated with an excess of an alkaline reagent, such as hydroxide, carbonate or alkoxide, containing the appropriate cation. Cations such as $NA^+$, $K^+$, $Ca^{+2}$ and $NH^{4+}$ are examples of cations present in pharmaceutically acceptable salts. Certain of the compounds form inner salts or zwitterions which may also be acceptable.

The compounds described above are useful for treating cell proliferation disorders, infectious diseases, and immunological diseases in mammals, and specifically, in human patients who require such treatment. Cell proliferative disorders that may be treated using the composition described above include cancer, cardiovascular disease such as myocarditis and restenosis following angioplasty, renal diseases such as lupus and polycystic kidney disease, host graft rejection, gout, and other proliferative disorders. Autoimmune diseases that may be treated with the compositions described above include rheumatoid arthritis, lupus, type I diabetes, multiple sclerosis and similar disorders and diseases. Infectious diseases that may be treated using the compositions described above include IBD, Crohn's disease, AIDS, ARDS, and similar disorders. The compositions disclosed above can also be used to treat fungal infections, dermatological diseases such as psoriasis, abnormal wound healing, keloids, immunological diseases such as autoimmunity, asthma, allergy, acute and delayed hypersensitivity, graft versus host disease, transplant rejection, and neuroimmunological disease such as multiple sclerosis and acute disseminated encephalomyelitis.

The method of treatment of these diseases and disorders comprises the administration parenterally, or orally of an effective quantity of the chosen compound or combinations thereof, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient. These dosage units may be administered one to ten times daily for acute or chronic disease. No unacceptable toxicological effects are expected when compounds of the invention are administered in accordance with the present invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration. It may be desirable to add excipients such as polyvinylpyrrolidinone, gelatin, hydroxycellulose, acacia, polyethylene glycol, mannitol, sodium chloride or sodium citrate. Alternatively, these compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dehydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is use, the preparation will be in the form of a syrup, elixir, emulsion or an aqueous or non-aqueous suspension. Such a liquid formulation may be administered directly p.o. or filled into a soft gelatin capsule.

EXAMPLE 1

The compounds useful in the therapeutic method of this invention are prepared by conventional methods of organic chemistry. Coupling reagents are well known in the art, such as DCC and other carbodiimides, EDC, BOP and PPA, and they may optionally be used with other reagents, such as HOBT, NMM and DMAP, which may facilitate the reaction. Preparation of compounds of the formula (1) wherein $D_1$, $D_2$ and E are amino acids are well known in the art using either conventional solution phase or solid phase techniques as described in Bodanszky, "The Practice of Peptide Synthesis," Springer-Verlag, First Edition, 1984. Suitable protective groups for the amino group are those disclosed by Greene et al., "Protective Group in Organic Synthesis," Second Edition, John Wiley and Sons, New York, 1991. The benzyloxycarbonyl, t-butoxycarbonyl and fluorenylmethoxycarbonyl groups are especially useful amino protecting groups.

Solid phase peptide synthesis was accomplished as follows. Rink amide resin is placed in a syringed fitted with a fritted filter. The resin is deprotected using 20% piperidine in DMF. After 20 minutes, the resin was washed five times with DMF, five times with methanol, then five times with DMF. A solution of amino acid (E), carbodiimide and HOBT in DMF was drawn up into the syringe and the reaction mixture was allowed to mix for 4 to 20 hours. The reaction solution was ejected and the mixture washed five times with DMF, five times with methanol, then five times with DMF. This cycle was repeated until the desired sequence was attached. The final coupling used, 5-methoxy-1-indanone-3-acetic acid, carbodiimide and HOBT. After final washings of the resin, the peptide fragment was cleaved from the resin using 95% TFA/5% water. Concentration of the cleavage mixture affords a white solid.

EXAMPLE 2

Compounds of this invention prepared according to the method of Example 1 were tested as follows. The 20S catalytic subunit of the proteasome (also known as the multicatalytic proteinase complex) was purified to homogeneity from bovine brain according to published methods (Wilk S. and Orlowski, M, 40 842 J. Neurochem (1983)). The chymotryptic activity of the complex is measured by the increase in fluorescence following cleavage of the substrate peptide succinyl-leucine-leucine-valine-tyrosine-7-amino-4-methyl coumarin. The standard in vitro assay consists of 2 μg 20S proteasome, 0.1–100 μg/ml proteasome inhibitor in 200 μl 50 mM HEPES, containing 0.1% sodium dodecyl sulphate, pH7.5. The proteolytic reaction is initiated by the addition of 50 μM fluorogenic peptide substrate and allowed to progress for 15 minutes at 37° C. The reaction is terminated by the addition of 100 μl of 100 mM acetate buffer, pH4.0. The rate of proteolysis is directly proportional to the amount of liberated aminomethylcoumarin which is measured by fluorescent spectroscopy (EX 370 nm, EM 430 nm). The structures of the compounds tested as well as the test results are reported in Table 2, below.

TABLE 2

| Compound | R3 | D1 | D2 | E | IC50 ug/ml |
|---|---|---|---|---|---|
| 1 | MeO | d-leu-NH2 | | | 5 |
| 2 | MeO | d-leu | d-leu-NH2 | | 1 |
| 3 | MeO | leu-NH2 | | | >10 |
| 4 | MeO | d-leu | his-NH2 | | >10 |
| 5 | MeO | leu | leu-NH2 | | >10 |
| 6 | MeO | d-leu | leu-NH2 | | >10 |
| 7 | MeO | leu | d-leu-NH2 | | >10 |
| 8 | MeO | Nle-NH2 | | | >10 |
| 9 | MeO | d-Nle-NH2 | | | >10 |
| 10 | MeO | Nva-NH2 | | | >10 |
| 11 | MeO | d-leu | Aib-NH2 | | >10 |
| 12 | MeO | d-phe-NH2 | | | >10 |
| 13 | MeO | CHA | Leu-NH2 | | >10 |
| 14 | MeO | phe | leu-NH2 | | >10 |
| 15 | MeO | Nle | d-Leu-NH2 | | >10 |
| 16 | MeO | Nle | leu-NH2 | | >10 |
| 17 | MeO | leu | leu | gly-NH2 | >10 |
| 18 | MeO | d-leu | leu | gly-NH2 | 5 |
| 19 | MeO | d-leu | d-leu | gly-NH2 | >10 |
| 20 | | | | | |
| 21 | MeO | leu | d-leu | gly-NH2 | 0.1 |
| 22 | MeO | d-Nle | d-leu-NH2 | | >10 |
| 23 | MeO | d-Nle | leu-NH2 | | >10 |
| 24 | MeO | phe-NH2 | | | >10 |
| 25 | MeO | Tic-NH2 | | | >10 |
| 26 | MeO | Tic | d-leu-NH2 | | >10 |
| 27 | MeO | d-phe | d-leu-NH2 | | 10 |

TABLE 2-continued

| Compound | R3 | D1 | D2 | E | IC50 ug/ml |
|---|---|---|---|---|---|
| 28 | MeO | leu | Aib-NH2 | | >10 |
| 29 | MeO | CHA-NH2 | | | >10 |
| 30 | MeO | d-val | d-leu-NH2 | | >10 |
| 31 | MeO | d-pro | d-leu-NH2 | | 10 |
| 32 | MeO | d-cha | d-leu-NH2 | | >10 |
| 33 | MeO | d-leu | d-val-NH2 | | >10 |
| 34 | MeO | d-val | d-val-NH2 | | >10 |
| 35 | MeO | d-cha | d-cha-NH2 | | >10 |
| 36 | MeO | d-phg-NH2 | | | >10 |
| 37 | MeO | d-phg | d-leu-NH2 | | >10 |
| 38 | MeO | benzyl | | | >10 |
| 39 | MeO | dibenzylamine | | | >10 |
| 40 | MeO | gly | gly | gly-NH2 | >10 |
| 41 | MeO | leu | gly | gly-NH2 | >10 |
| 42 | MeO | gly | d-leu | gly-NH2 | >10 |
| 43 | MeO | nle | d-leu | gly-NH2 | >10 |
| 44 | MeO | nva | d-leu | gly-NH2 | >10 |
| 45 | MeO | phe | d-leu | gly-NH2 | >10 |
| 46 | MeO | cha | d-leu | gly-NH2 | >10 |
| 47 | MeO | val | d-leu | gly-NH2 | >10 |
| 48 | MeO | phg | d-leu | gly-NH2 | >10 |
| 49 | MeO | pro | d-leu | gly-NH2 | >10 |
| 50 | MeO | leu | d-leu | gly-NH2 | 0.5 |
| 51 | MeO | leu | d-leu | gly-NH2 | 0.5 |
| 52 | MeO | d-leu | ala-NH2 | | >10 |
| 53 | MeO | d-leu | d-ala-NH2 | | >10 |
| 54 | MeO | d-leu | d-pro-NH2 | | >10 |
| 55 | MeO | d-pro-NH2 | | | >10 |
| 56 | MeO | d-leu | d-phe-NH2 | | >10 |
| 57 | MeO | d-nva | d-leu-NH2 | | >10 |
| 58 | MeO | nva | d-leu-NH2 | | >10 |
| 59 | MeO | d-ala | d-leu-NH2 | | >10 |
| 60 | MeO | d-tic | d-leu-NH2 | | >10 |
| 61 | MeO | d-ser | d-leu-NH2 | | >10 |
| 62 | MeO | diisopropyl | | | >10 |
| 63 | MeO | morpholine | | | >10 |
| 64 | MeO | pyrrolidine | | | >10 |
| 65 | MeO | phenethylamine | | | >10 |
| 66 | MeO | phenpropla mine | | | >10 |
| 67 | MeO | piperidine | | | >10 |
| 68 | MeO | diethylamine | | | >10 |
| 69 | MeO | cyclobutylamine | | | >10 |
| 70 | MeO | heptylamine | | | >10 |
| 71 | MeO | 3-methoxypropylamine | | | >10 |
| 72 | MeO | 3,4-dimethoxyphenyethylaime | | | >10 |
| 73 | MeO | N-methylbenzylamine | | | >10 |
| 74 | MeO | cyclopentylamine | | | >10 |
| 75 | MeO | 2,6-dimethylpiperidine | | | >10 |
| 76 | MeO | N-benzylethanolamine | | | >10 |
| 77 | MeO | indoline | | | >10 |
| 78 | MeO | dimethylamine | | | >10 |
| 79 | MeO | bis(2-methoxyethyl)amine | | | >10 |
| 80 | MeO | piperonylamine | | | >10 |
| 81 | MeO | 4-hydroxypiperidine | | | >10 |
| 82 | MeO | 3-iodoaniline | | | >10 |
| 83 | MeO | 1-aminoindane | | | >10 |
| 84 | MeO | ethanolamine | | | >10 |
| 85 | MeO | 4- | | | >10 |

TABLE 2-continued

| Compound | R3 | D1 | D2 | E | IC50 ug/ml |
|---|---|---|---|---|---|
| | | methoxybenzylamine | | | |
| 86 | MeO | leu | d-nle | gly-NH2 | >10 |
| 87 | MeO | leu | d-nva | gly-NH2 | >10 |
| 88 | MeO | leu | d-phe | gly-NH2 | >10 |
| 89 | MeO | leu | d-cha | gly-NH2 | >10 |
| 90 | MeO | leu | d-val | gly-NH2 | >10 |
| 91 | MeO | leu | d-phg | gly-NH2 | 10 |
| 92 | MeO | leu | d-pro | gly-NH2 | >10 |
| 93 | MeO | d-arg | d-leu-NH2 | | >10 |
| 94 | MeO | d-asp | d-leu-NH2 | | >10 |
| 95 | MeO | d-asn | d-leu-NH2 | | 10 |
| 96 | MeO | d-asn | d-leu-NH2 | | >10 |
| 97 | MeO | d-glu | d-leu-NH2 | | >10 |
| 98 | MeO | d-gln | d-leu-NH2 | | |
| 99 | MeO | d-his | d-leu-NH2 | | >10 |
| 100 | MeO | d-lys | d-leu-NH2 | | >10 |
| 101 | MeO | d-thi | d-leu-NH2 | | >10 |
| 102 | MeO | d-tyr | d-leu-NH2 | | >10 |
| 103 | MeO | d-trp | d-leu-NH2 | | >10 |
| 104 | MeO | 4-(aminomethyl)pyridine | | | >10 |
| 105 | MeO | 1,2-diaminopropane | | | >10 |
| 106 | MeO | thiomorpholine | | | >10 |
| 107 | MeO | 2-methoxybenzylamine | | | >10 |
| 108 | MeO | 4-methylpiperidine | | | >10 |
| 109 | MeO | 3-pyrrolidinol | | | >10 |
| 110 | MeO | 4-amino-1-benzylpiperidine | | | >10 |
| 111 | MeO | 3-amino-1,2-propandiol | | | >10 |
| 112 | MeO | 1-(2-aminoethyl)pyrrolidine | | | >10 |
| 113 | MeO | 2-amino-2-methyl-1-propanol | | | >10 |
| 114 | MeO | 2-(amionmethyl)pyridine | | | >10 |
| 115 | MeO | 2-(methylamio)ethanol | | | >10 |
| 116 | MeO | 3-(3-pyridylmethyiamio)propionitrile | | | >10 |
| 117 | MeO | 2-methyoxethylamine | | | >10 |
| 118 | MeO | 2-amino-1-phenyl-1,3-propanediol | | | >10 |
| 119 | MeO | 2-pyrrolidinomethanol | | | >10 |
| 120 | MeO | 3-phenyl-1-propylamine | | | >10 |
| 121 | MeO | p-anisidine | | | >10 |
| 122 | MeO | aniline | | | >10 |
| 123 | MeO | leu | d-leu | d-val-NH2 | >10 |
| 124 | MeO | leu | d-leu | val-NH2 | >10 |
| 125 | MeO | leu | d-leu | d-ala-NH2 | >10 |
| 126 | MeO | leu | d-leu | ala-NH2 | >10 |
| 127 | MeO | leu | d-leu | d-phe-NH2 | >10 |
| 128 | MeO | leu | d-leu | phe-NH2 | >10 |
| 129 | MeO | d-leu | d-arg-NH2 | | >10 |

TABLE 2-continued

| Compound | R3 | D1 | D2 | E | IC50 ug/ml |
|---|---|---|---|---|---|
| 130 | MeO | d-leu | d-asp-NH2 | | >10 |
| 131 | MeO | d-leu | d-asn-NH2 | | >10 |
| 132 | MeO | d-leu | d-cha-NH2 | | >10 |
| 133 | MeO | d-leu | d-glu-NH2 | | >10 |
| 134 | MeO | d-leu | d-nle-NH2 | | >10 |
| 135 | MeO | d-leu | d-tyr-NH2 | | >10 |
| 136 | MeO | d-leu | d-trp-NH2 | | >10 |
| 137 | MeO | d-leu | d-gln-NH2 | | >10 |
| 138 | MeO | d-leu | d-lys-NH2 | | >10 |
| 139 | MeO | d-leu | d-nva-NH2 | | >10 |
| 140 | MeO | d-leu | d-phg-NH2 | | >10 |
| 141 | MeO | d-leu | d-ser-NH2 | | >10 |
| 142 | MeO | d-leu | d-thi-NH2 | | >10 |
| #43 | MeO | d-leu | d-tic-NH2 | | >10 |
| 144 | MeO | N-(4-hydroxyphenyl)-2-napthylamine | | | >10 |
| 145 | MeO | 2-amino-4,6-dihydroxy-5-methylpyrimidine | | | >10 |
| 146 | MeO | 5-(hydroxymethyl)-2-pyrrolidinone | | | >10 |
| 147 | MeO | 3-hydroxydiphenylamine | | | >10 |
| 148 | MeO | 2-amino-4-phenylphenol | | | >10 |
| 149 | MeO | 2-(4-methoxybenzylamino)pyridine | | | >10 |
| 150 | MeO | hexamethylenediamine | | | >10 |
| 151 | MeO | 4-hydroxy-4-phenylpiperidine | | | >10 |
| 152 | MeO | 4-iodoaniline | | | >10 |
| 153 | MeO | 2-methyl-6-nitroaniline | | | >10 |
| 154 | MeO | (r)-(-)-5-(hydroxymethyl)-2-pyrrolidinone | | | >10 |
| 155 | MeO | 2-amino-4-chloro-6-methyl-pyrimidine | | | >10 |
| 156 | MeO | 2-amino-5-chloropyridine | | | >10 |
| 157 | MeO | 3,4-dichloroaniline | | | >10 |
| 158 | MeO | 4-amino-2-mercaptopyrimidine | | | >10 |
| 159 | H | leu | d-leu | gly-NH2 | |
| 160 | MeO | indoline | | | >10 |
| 161 | MeO | phenpropyl | | | >50 |
| 162 | MeO | p-anisidine | | | >50 |
| 163 | MeO | piperonyl | | | >50 |
| 164 | MeO | 2-pyrrolidine-methanol | | | >50 |
| 165 | MeO | 2-amino-1-phenyl-1,3-propanediol | | | >50 |
| 166 | MeO | N-benzyl-ethanolamine | | | >50 |
| 167 | MeO | dimethylamide | | | >50 |
| 168 | MeO | anilino | | | >50 |
| 169 | MeO | bis-2- | | | >50 |

TABLE 2-continued

| Compound | R3 | D1 | D2 | E | IC50 ug/ml |
|---|---|---|---|---|---|
| | | methoxyethyl amine | | | |
| 170 | MeO | leu | d-leu | aib-NH2 | >10 |
| 171 | MeO | leu | d-leu-OH | | >10 |
| 172 | MeO | leu | d-leu-OH | | >10 |
| 173 | MeO | leu | d-leu | benzyl | 0.5 |
| 174 | MeO | leu | d-leu | morpholine | >10 |
| 175 | MeO | leu | d-leu | piperdinyl | >10 |
| 176 | MeO | leu | d-leu | pyrrolidino | >10 |
| 177 | MeO | leu | d-leu | dibenzyl | 1 |
| 178 | MeO | leu | d-leu | hydroxyethyl | >10 |
| 179 | MeO | leu | d-leu | N-methylbenzyl | >10 |
| 180 | MeO | leu | d-leu | N-methylbenzyl | >10 |
| 181 | MeO | Aminomethyl cyclohexanea mide | | | >10 |
| 182 | MeO | leu | aminomethylcyclohexaneamide | | >10 |
| 183 | MeO | leu | aminomethylcyclo hexaneamide | gly-NH2 | >10 |
| 184 | MeO | leu | d-leu | phenyl | >10 |
| 185 | MeO | leu | d-leu | phenethyl | >10 |
| 186 | MeO | leu | d-leu | phenpropyl | >10 |
| 187 | MeO | leu | d-leu | indane | 0.5 |
| 188 | MeO | leu | d-leu | aminomethylcyclohe xane | >10 |
| 189 | MeO | leu | d-leu | aminomethylpyridin e | >10 |
| 190 | MeO | leu | d-leu | adamantyl | >10 |
| 191 | MeO | leu | d-leu | tetrahydroisoquinoli ne | >10 |
| 192 | MeO | leu | d-leu | 4-pyridylmethyl | 10 |
| 193 | MeO | leu | d-leu | N-benzylhydroxami e | 0.4 |
| 194 | MeO | leu | d-leu | 4-methoxybenzyl | >10 |
| 195 | MeO | leu | d-leu | 4-nitrobenzyl | 10 |
| 196 | MeO | leu | d-leu | 2,6-difluorobenzyl | 0.08 |
| 197 | MeO | leu | d-leu | piperonyl | 0.2 |
| 198 | MeO | d-leu | benzyl | | >10 |
| 199 | MeO | d-leu | dibenzyl | | >10 |
| 200 | MeO | d-leu | isoamyl | | >10 |

EXAMPLE 3

Compounds prepared according to the method of Example 1 were assayed against several different cell lines. Cell monolayers were cultured in the presence of test compound for 18 hours to assess their ability to inhibit cell proliferation. Cell proliferation was determined calorimetrically using the Celltiter 96 Aqueous non-radioactive cell proliferation assay (Promega) where cell proliferation is directly proportional to absorbance at 490 nm. Results are quoted as the $IC_{50}$ in $\mu g/ml$ for inhibition of cell proliferation in various cell types.

| Compound | RAW | MCF-7 | OVCAR | CaCo | Panc-I |
|---|---|---|---|---|---|
| 173 | 20 | 10 | 8 | 17 | 17 |
| 187 | 10 | 6 | 5 | 8 | 7 |
| 194 | 1 | | 3 | | 8 |
| 196 | 7 | | 2 | | 8 |
| 197 | 12 | | 2 | | 8 |

EXAMPLE 4

Compounds prepared according to the method of Example 1 were tested for the inhibition of LPS induced TNF synthesis. RAW cells were pretreated with different concentrations of test compound for 1 hour prior to the administration of lipopolysaccharide (100 ng/ml). Cell culture supernatants were harvested after 1 hour and assayed for TNF concentration by ELISA (Biosource)

| Compound | $IC_{50}$ ($\mu g/ml$) |
|---|---|
| 173 | 5 |
| 187 | 5 |
| 194 | 3 |
| 196 | 3 |
| 197 | 3 |

EXAMPLE 5

This Example examines the ability of compound 173 and particularly compound 187 described in Tables 1 & 2 above to inhibit proteasome activity as indicated, in part, by the presence of IκB and/or p105 in inhibited cells. In order for NF-κB to translocate to the nucleus in response to a stimulus such as lipopolysaccharide (LPS) and activate transcription two proteolytic events need to occur, namely degradation of the inhibitory protein IκB and processing of p105 to p50. These proteolytic events serve to unmask the nuclear localization signal of NF-κB.

Inhibition of LPS-induced IκB Degradation

Figure 1:
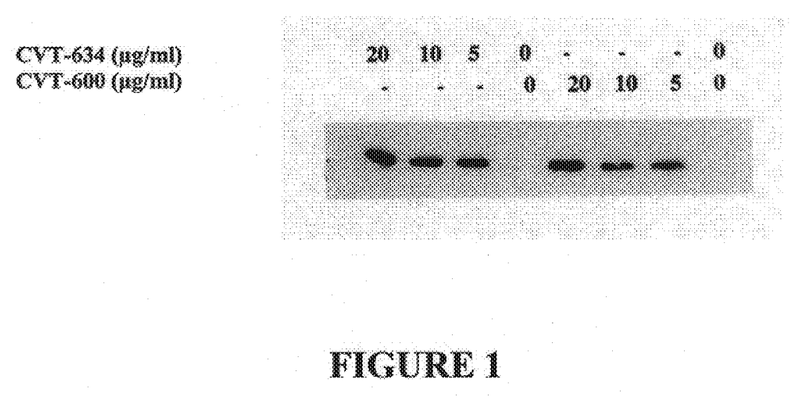
FIG. 1 is a Western Blot immunoreactivity assay using an anti-IκBα antibody of RAW cell extract which had been treated with compounds 173 and 187 which are described in Tables 1 and 2.

RAW cells were pretreated with different concentrations of test compound for 1 hour prior to the administration of lipopolysaccharide (100 ng/ml). Whole cell lysates were harvested after 1 hour, 10 μg protein was separated by SDS-PAGE, transferred to nitrocellulose and assayed for immunoreactivity with anti-IκBa antibody. Western blots, (See FIG. 1), were visualized using the Boehringer Mannheim Chemiluminescent detection kit. The blot shows that IκB is present in cells treated with as little as 5 μg/ml of compounds 173 and 187.

Inhibition of LPS-induced p150 to p50 Processing

Figure 2:
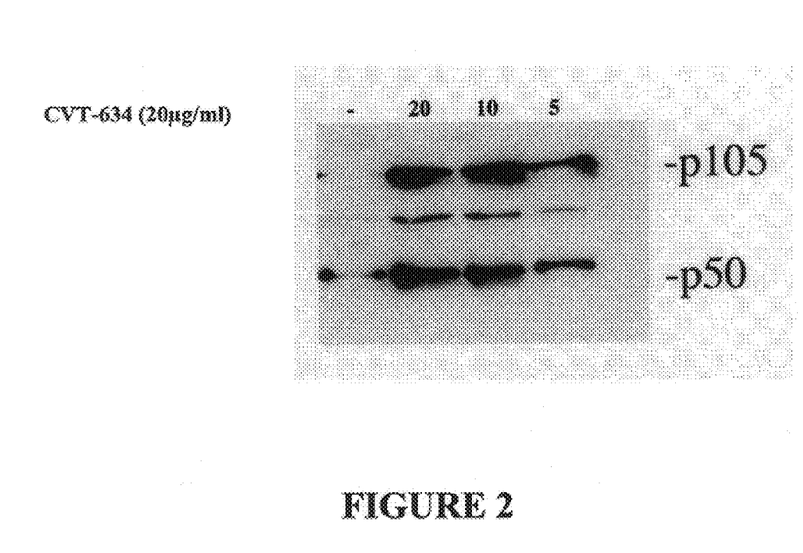
FIG. 2 is a Western Blot immunoreactivity assay towards an anti-P50 antibody of RAW cell extracts which had been treated with compound 187, which is described in Tables 1 and 2, prior to exposure to LPS.

Compound 187 as described in Tables 1 & 2 above was used to pretreat RAW cells as described above, and whole cell lysates prepared as described above were analyzed for immunoreactivity toward an anti-p50 antibody. The results, set forth in FIG. 2 indicate that p50 and p150 are both present in cells treated with as little as 5 μg/ml of compound 187, while in untreated cells, majority of P105 has been processed to p50.

Figure 3:
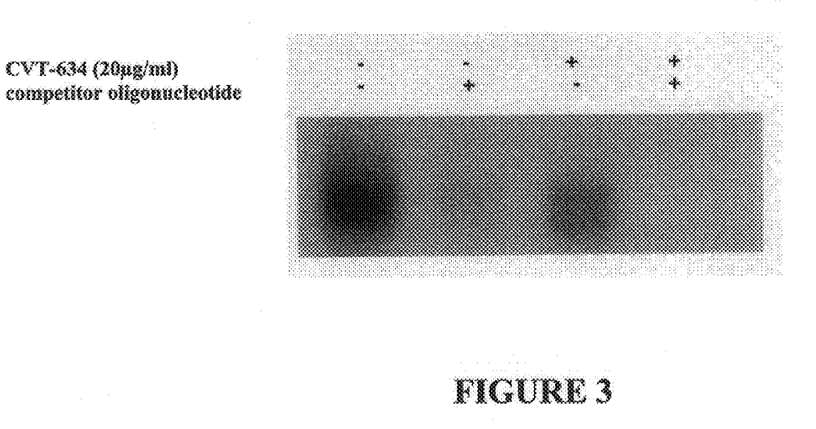
FIG. 3 is a gel mobility shift assay using nuclear extract prepared from RAW cells that had been pretreated with compound 187, which is described in Tables 1 and 2, prior to exposure to LPS.

Inhibition of LPS-induced Translocation of NF-κB to the Nuclear Fraction of the Cell RAW cells were treated for 1 hour with compound 187 (20 μg/ml) and then incubated with lipopolysaccharide (100 ng/ml) for a further one hour. Nuclear fractions were prepared according to standard procedures. Binding reactions for gel mobility shift assays contained 5 μg of nuclear extract protein, 50,000 cpm of $^{32}$P-labeled NF-κB consensus binding oligonucleotide in the presence and absence of a fifty fold excess of unlabeled oligonucleotide. The gel mobility shift assay, set forth in FIG. 3 shows that compound 187 is effective in inhibiting the accumulation of NF-κB in the nucleus of cells.

What is claimed is:

1. Compositions having the formula:

wherein $R_1$–$R_2$ and $R_4$–$R_9$ are each hydrogen and $R_3$ is —OCH$_3$; X is wherein $D_1$ and $D_2$ are each amino acids; and E is an amino acid or —N—$R_{15}$ wherein $R_{15}$ is selected from the group of compounds selected from hydrogen, lower alkyl, substituted lower alkyl, aryl, substituted aryl, and aralkyl.

2. The compounds of claim 1 wherein $D_1$ and $D_2$ are each selected from -leu or D-leu.

3. The compounds of claim 1 wherein E is selected from gly-NH$_2$, hydrogen, benzyl, dibenzyl, indane, n-benzylhydroxamine, 2,6-difluorobenzyl, and piperonyl.

4. Compositions having the formula:

wherein $R_1$ is isopropyl, benzyl, hydroxyethyl, adamantyl, phenyl, phenethyl, or chclohexylmethyl, and $R_2$ is hydrogen or methyl.

5. The compounds of claim 1 wherein $R_1$ is benzyl and $R_2$ is hydrogen.

6. The compositions of claim 1 wherein $R_1$ and $R_2$ are each selected from the group including hydrogen, 1-indanyl, piperonyl, 2-6-difluorobenzyl, indane, benzyl, dibenzyl, 4-methoxybenzyl, 4-nitrobenzyl, pentafluorobenzyl, furfuryl, diphenylmethyl, 4-phenylbenzyl, 2-phenylbenzyl, 4-benzyloxybenzyl, and benzofurfuryl.

7. Composition having the formula:

8. The compositions of claim 7 wherein R is 1-indanyl, piperonyl, 2-6-difluorobenzyl, indane, benzyl, dibenzyl, 4-methoxybenzyl, 4-nitrobenzyl, pentafluorobenzyl, furfuryl, diphenylmethyl, 4-phenylbenzyl, 2-phenylbenzyl, 4-benzyloxybenzyl, and benzofurfuryl.

9. The compositions of claim 7 wherein R is 2,6-difluorobenzyl.

* * * * *